United States Patent
Beaussoubre et al.

(10) Patent No.: US 11,772,067 B2
(45) Date of Patent: Oct. 3, 2023

(54) ODOR NEUTRALIZER FOR AMMONIA AND PRIMARY OR SECONDARY AMINES

(71) Applicant: FIRMENICH SA, Satigny (CH)

(72) Inventors: Pascal Beaussoubre, Geneva (CH); Wolfgang Fieber, Geneva (CH)

(73) Assignee: FIRMENICH SA, Satigny (CH)

(*) Notice: Subject to any disclaimer, the term of this patent is extended or adjusted under 35 U.S.C. 154(b) by 686 days.

(21) Appl. No.: 16/605,397

(22) PCT Filed: Apr. 25, 2018

(86) PCT No.: PCT/EP2018/060571
§ 371 (c)(1),
(2) Date: Oct. 15, 2019

(87) PCT Pub. No.: WO2018/197549
PCT Pub. Date: Nov. 1, 2018

(65) Prior Publication Data
US 2020/0047152 A1    Feb. 13, 2020

(30) Foreign Application Priority Data

Apr. 27, 2017 (EP) .................................... 17168502

(51) Int. Cl.
*B01J 20/10* (2006.01)
*B01D 53/04* (2006.01)
*B01J 20/26* (2006.01)

(52) U.S. Cl.
CPC ............ *B01J 20/103* (2013.01); *B01D 53/04* (2013.01); *B01J 20/262* (2013.01); *B01D 2253/106* (2013.01); *B01D 2257/406* (2013.01)

(58) Field of Classification Search
CPC ....... B01J 20/103; B01J 20/262; B01D 53/04; B01D 2253/106; B01D 2257/406
See application file for complete search history.

(56) References Cited

U.S. PATENT DOCUMENTS

| | | | |
|---|---|---|---|
| 6,015,550 | A | 1/2000 | Marquis |
| 6,015,555 | A | 1/2000 | Friden |
| 2005/0084438 | A1 | 4/2005 | Do et al. |
| 2008/0311069 | A1 | 12/2008 | Williams et al. |

(Continued)

FOREIGN PATENT DOCUMENTS

| | | | | |
|---|---|---|---|---|
| EP | 1145723 A2 | * | 10/2001 | ............. A01N 25/08 |
| EP | 1145723 A2 | | 10/2001 | |
| EP | 2524704 A2 | | 11/2012 | |

(Continued)

OTHER PUBLICATIONS

Hosgor et al. (Preparation and characterization of phosphine oxide based polyurethane/silica nanocomposite via non-isocyanate route, 2010, Progress in Organic Coatings vol. 69, pp. 366-375) (Year: 2010).*

(Continued)

*Primary Examiner* — Youngsul Jeong

(57) ABSTRACT

Described herein is a method of using solid particles having a surface functionalized with a terminal cyclocarbonate group to neutralize an odor from ammonia and primary or secondary amines. Also described herein are perfuming compositions and perfuming consumer products that include malodor neutralizers.

11 Claims, 3 Drawing Sheets

(56) References Cited

U.S. PATENT DOCUMENTS

2009/0217465 A1* 9/2009 Cremer ................ C09C 1/3081
8/405

FOREIGN PATENT DOCUMENTS

| JP | H02302258 A | 12/1990 |
|----|-------------|---------|
| JP | 2014501233 A | 1/2014 |
| WO | 1999046350 A1 | 9/1999 |
| WO | 2008155683 A1 | 12/2008 |
| WO | 2017085152 A1 | 5/2017 |

OTHER PUBLICATIONS

Brinker, "Hydrolysis and Condensation of Silicates: Effects on Structure", Journal of Non-Crystalline Solids, Published Mar. 1988, pp. 31-50, vol. 100.

Hosgor et al., "Preparation and Characterization of Phosphine Oxide Based Polyurethane/Silica Nanocomposite via Non-isocyanate Route," Progress in Organic Coatings, Published 2010, pp. 366-375, vol. 69.

Kathalewar et al., "Effect of Incorporation of Surface Treated Zinc Oxide on Non-isocyanate Polyurethane Based Nano-composite Coatings," Progress in Organic Coatings, Published 2013, pp. 1215-1229, vol. 76.

Kim et al., "Capillary Condensation onto Titania (TiO2) Nanoparticle Agglomerates," Langmuir, Published Jan. 23, 2007, pp. 2497-2504, vol. 23, No. 5.

International Search Report and Written Opinion for International Application No. PCT/EP2018/060571, dated Sep. 11, 2018, 12 pages.

* cited by examiner

ODOR NEUTRALIZER FOR AMMONIA AND PRIMARY OR SECONDARY AMINES

CROSS REFERENCE TO RELATED APPLICATIONS

This application is a U.S. National Phase Application of PCT/EP2018/060571, filed on Apr. 25, 2018, which claims the benefit of priority to European Patent Application Serial No. 17168502.7, filed Apr. 27, 2017, the entire contents of which is hereby incorporated by reference in its entirety.

FIELD

The present invention relates to the field of perfumery and more particularly to the fields of malodor counteractancy. In particular, it relates to the use of solid particles having a surface functionalized with terminal cyclocarbonate groups to neutralize malodor, in particular from ammonia and primary or secondary amines Perfuming compositions and perfuming consumer products comprising those solid particles are also objects of the present invention.

BACKGROUND

Offensive odors known as malodors are largely present in the surrounding environment and are constituted of complex mixtures of volatile organic compounds. The composition of malodors depends on the source generating them such as sweat, garbage, bathroom, kitchen, pet waste, waste water plant or body odor. These volatile organic compounds belong to different chemical families, including amines, carboxylic acids, alcohols, aldehydes and ketones or thiols, sulfides and disulfides.

The multiplicity of chemical constituents of malodor complex mixtures and the variety of sources of malodors has led to the development of different methods to reduce or suppress the malodor perception. These methods can be divided in three groups corresponding to different approaches. The first one addresses prevention of malodor formation, e.g. by using antimicrobial compounds which aim at suppressing or reducing the activity of microorganisms at the origin of malodor generation. The second approach relates to the sensory modification of the malodors, by using perfumery ingredients to cover them. The third approach tackles the elimination or neutralization of the malodors, e.g. by using an ingredient which will chemically and/or physico-chemically interact with the malodor compounds.

This latter method has been, among other, used to overcome malodors generated by ammonia and amine-containing compounds which are found in a large amount of malodor complex mixtures, typically in kitchen, garbage or bathroom.

U.S. Pat. No. 6,015,555 states "[t]his invention concerns a method useful for reducing odor where odoriferous amine-containing compound is present, comprising: applying an alkylene carbonate to a source of the amine-containing compound under conditions such that the alkylene carbonate forms a reaction product with odoriferous amine-containing compounds such that odor is reduced."

International Patent Application Publication No. WO1999046350A1 states "[t]his invention is directed to a novel biological deodorizing liquid composition which is designed to be applied in the areas of pet care, toilet care, carpet care, and garbage collections or processes, management of industrial wastes, including sludge processing, landfill and composting, and odor control of livestock production processes and other organic wastes."

However, there is still a need to provide compositions to irreversibly reduce the perceived malodor from ammonia and primary or secondary amines.

SUMMARY

The invention relates to the use of solid particles having a surface functionalized with terminal cyclocarbonate groups to neutralize malodor, in particular, malodors generated by ammonia and primary amines or secondary amines Unexpectedly, it has been found that the solid particles according to the present invention are particularly efficient in reacting with the ammonia and primary amines or secondary amines that cause malodor, and thus, eliminate the related malodor irreversibly.

In one embodiment, the present invention provides solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I):

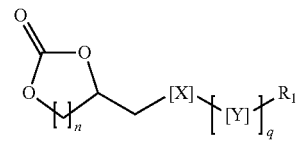

wherein:
n=1 or 2;
[X] is an element selected from the group consisting of O, N and C;
[Y] represents an alkylene group carrying 1-20 C atoms, that can be linear, branched, or cyclic, or connected to a carbonyl or an ether group;
q=0 or 1
$R_1$ is a coupling reactive group serving as a linker selected from silanes, siloxanes, phosphates or carboxylates.

In one embodiment, n=1, [X] is O, [Y] is propylene, q=1, and $R_1$ is tri(m)ethoxysilane.

In one embodiment the at least one terminal cyclocarbonate group attached to the surface via a linker is a single structure. In an alternate embodiment, the at least one terminal cyclocarbonate group attached to the surface via a linker is more than one structure.

In one embodiment, the present invention provides a composition comprising:
a) the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I); and
b) at least one ingredient selected from the group consisting of a carrier, a perfumery ingredient, a perfumery adjuvant and a mixture thereof;
wherein the composition neutralizes malodors produced from ammonia, primary amines and/or secondary amines.

In one embodiment, the composition further comprises a malodor counteracting composition.

In one embodiment, the composition is formulated as a consumer product, wherein the consumer product neutralizes malodors produced from ammonia, primary amines and/or secondary amines.

In one embodiment, the present invention provides a method to neutralize malodors produced from ammonia, primary amines and/or secondary amines, comprising, dispensing into a closed space in need thereof, an effective amount of the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I).

In one embodiment, the present invention provides a method to neutralize malodors produced from ammonia, primary amines and/or secondary amines, comprising, dispensing into a closed space in need thereof, an effective amount of a composition comprising:
a) the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I); and
b) at least one ingredient selected from the group consisting of a carrier, a perfumery ingredient, a perfumery adjuvant and a mixture thereof.

In one embodiment, the present invention provides a method to neutralize malodors produced from ammonia, primary amines and/or secondary amines, comprising, applying to a surface in need thereof, an effective amount of solid particles having a surface functionalized with a terminal cyclocarbonate group having at least one structure set forth in formula (I).

In one embodiment, the present invention provides a method to neutralize malodors produced from ammonia, primary amines and/or secondary amines, comprising, applying to a surface in need thereof, an effective amount of a composition comprising:
a) the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I); and
b) at least one ingredient selected from the group consisting of a carrier, a perfumery ingredient, a perfumery adjuvant and a mixture thereof.

DETAILED DESCRIPTION

Figure 1:
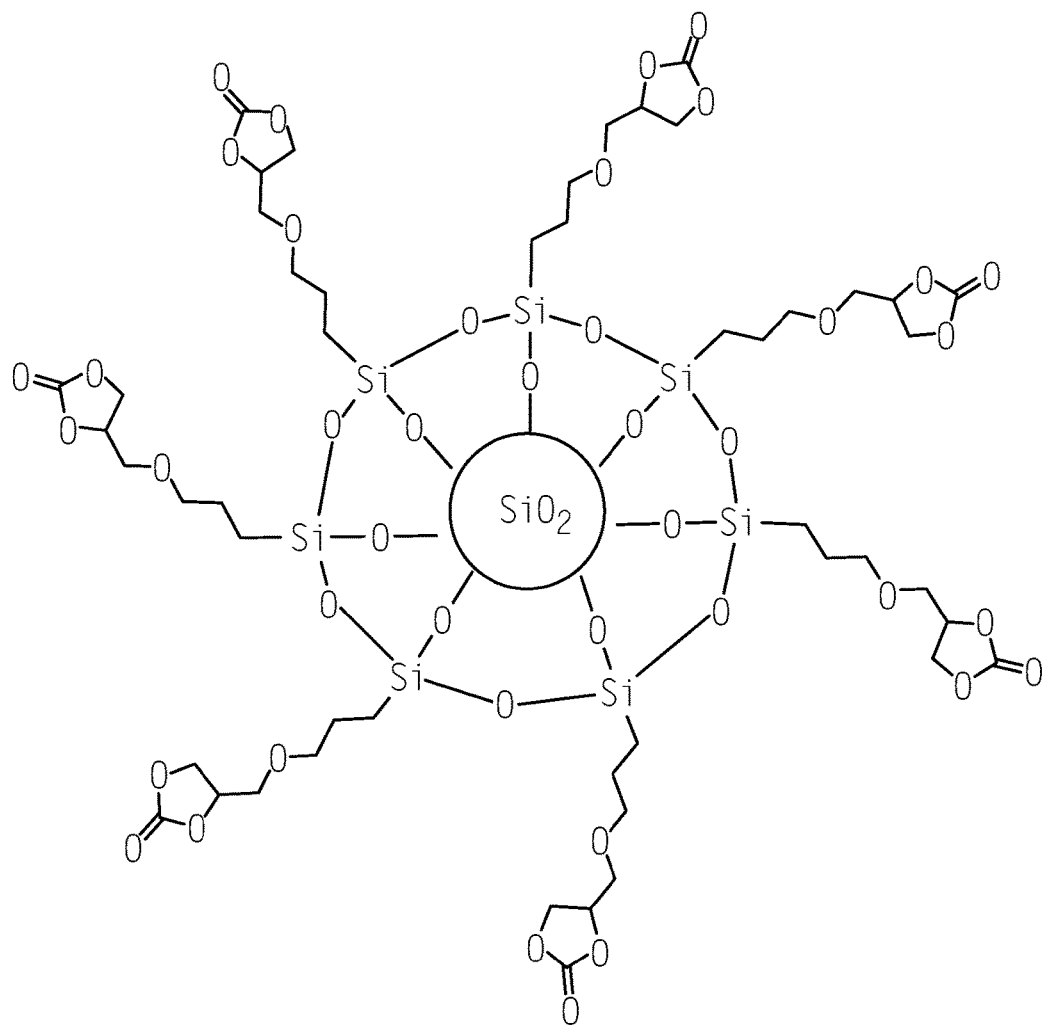
FIG. 1 shows a representation of a solid particle having a surface functionalized with terminal cyclocarbonate groups according to some embodiments of the present invention.

The invention relates to the use of solid particles having a surface functionalized with terminal cyclocarbonate groups to neutralize malodor, in particular, malodors generated by ammonia and primary amines or secondary amines Unexpectedly, it has been found that the solid particles according to the present invention are particularly efficient in reacting with the ammonia and primary amines or secondary amines that cause malodor, and thus, eliminate the related malodor irreversibly.

As used herein, the term "functionalized" refers to the chemical modification of the surface of the solid particles by the covalent addition of chemical moieties that impart chemical properties to the surface of the solid particles that are different to the chemical properties of the original surface of the solid particles.

The Terminal Cyclocarbonate Structures Suitable for use in Some Embodiments of the Present Invention In one embodiment, the present invention provides solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I):

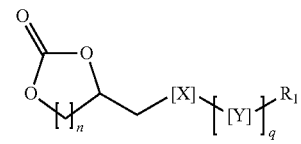

wherein:
n=1 or 2;
[X] is an element selected from the group consisting of O, N and C;
[Y] represents an alkylene group carrying 1-20 C atoms, that can be linear, branched, or cyclic, or connected to a carbonyl or an ether group;
q=0 or 1
$R_1$ is a coupling reactive group serving as a linker selected from silanes, siloxanes, phosphates or carboxylates.

In one embodiment, n=1, [X] is O, [Y] is propylene, q=1, and $R_1$ is tri(m)ethoxysilane.

In one embodiment the at least one terminal cyclocarbonate group attached to the surface via a linker is a single structure. In an alternate embodiment, the at least one terminal cyclocarbonate group attached to the surface via a linker is more than one structure.

In some embodiments, the terminal cyclocarbonate groups of formula (I) are commercially available or can be obtained by esterification or etherification of 4-(hydroxymethyl)-1,3-dioxolan-2-one using methods known by the person skilled in the art.

The Solid Particles Suitable for use in Some Embodiments of the Present Invention In one embodiment, the solid particle is an oxide of an element selected from the group of Si, Ti, Fe, Zn and Al.

The average diameter of the solid particles can range from 200 nm to 10 µm, or greater. In one embodiment, the average diameter of the solid particles ranges from 200 nm to 10 mm. In one embodiment, the average diameter of the solid particles is 200 nm. In an alternate embodiment, the average diameter of the solid particles is 500 nm. In an alternate embodiment, the average diameter of the solid particles is 1 µm. In an alternate embodiment, the average diameter of the solid particles is 1.5 µm. In an alternate embodiment, the average diameter of the solid particles is 2 µm. In an alternate embodiment, the average diameter of the solid particles is 2.5 µm. In an alternate embodiment, the average diameter of the solid particles is 3 µm. In an alternate embodiment, the average diameter of the solid particles is 3.5 µm. In an alternate embodiment, the average diameter of the solid particles is 4 µm. In an alternate embodiment, the average diameter of the solid particles is 4.5 µm. In an alternate embodiment, the average diameter of the solid particles is 5 µm. In an alternate embodiment, the average diameter of the solid particles is 4.5 µm. In an alternate embodiment, the average diameter of the solid particles is 5 µm. In an alternate embodiment, the average diameter of the solid particles is 5.5 µm. In an alternate embodiment, the average diameter of the solid particles is 6 µm. In an alternate embodiment, the average diameter of the solid particles is 6.5 µm. In an alternate embodiment, the average diameter of the solid particles is 7 µm. In an alternate embodiment, the average diameter of the solid particles is 7.5 µm. In an alternate embodiment, the average diameter of the solid particles is 8 µm. In an alternate embodiment, the average diameter of the solid particles is 8.5 µm. In an alternate embodiment, the average diameter of the solid particles is 9 µm. In an alternate embodiment, the average diameter of the solid particles is 9.5 µm. In an alternate embodiment, the average diameter of the solid particles is 10 µm. In an alternate embodiment, the average diameter of the solid particles is 50 µm. In an alternate embodiment, the average diameter of the solid particles is 100 µm. In an alternate embodiment, the average diameter of the solid particles is 150 µm. In an alternate embodiment, the average diameter of the solid particles is 200 µm. In an alternate embodiment, the average diameter of the solid particles is 250 µm. In an alternate embodiment, the average diameter of the solid particles is 300 µm. In an alternate embodiment, the average diameter of the solid particles is 350 µm. In an alternate embodiment, the average diameter of the solid particles is 400 µm. In an alternate embodiment, the average diameter of the solid particles is 450 µm. In an alternate embodiment, the average diameter of the solid particles is 500 µm. In an alternate embodiment, the average diameter of the solid particles is 550 µm. In an alternate embodiment, the average diameter of the solid particles is 600 µm. In an alternate embodiment, the average diameter of the solid particles is 700 µm. In an alternate embodiment, the average diameter of the solid particles is 800 µm. In an alternate embodiment, the average diameter of the solid particles is 900 µm. In an alternate embodiment, the average diameter of the solid particles is 1 mm. In an alternate embodiment, the average diameter of the solid particles is 2 mm. In an alternate embodiment, the average diameter of the solid particles is 3 mm. In an alternate embodiment, the average diameter of the solid particles is 4 mm. In an alternate embodiment, the average diameter of the solid particles is 5 mm. In an alternate embodiment, the average diameter of the solid particles is 6 mm. In an alternate embodiment, the average diameter of the solid particles is 7 mm. In an alternate embodiment, the average diameter of the solid particles is 8 mm. In an alternate embodiment, the average diameter of the solid particles is 9 mm. In an alternate embodiment, the average diameter of the solid particles is 10 mm.

In one embodiment, the solid particle is an oxide of an element selected from the group of Si, Ti, Fe, Zn and Al. In some embodiments, the solid particles aggregate. The average diameter of the aggregate can range from 200 nm to 10 µm, or greater. In one embodiment, the average diameter of the aggregate ranges from 200 nm to 10 mm. In one embodiment, the average diameter of the aggregate is 200 nm. In an alternate embodiment, the average diameter of the aggregate is 500 nm. In an alternate embodiment, the average diameter of the aggregate is 1 µm. In an alternate embodiment, the average diameter of the aggregate is 1.5 µm. In an alternate embodiment, the average diameter of the aggregate is 2 µm. In an alternate embodiment, the average diameter of the aggregate is 2.5 µm. In an alternate embodiment, the average diameter of the aggregate is 3 µm. In an alternate embodiment, the average diameter of the aggregate is 3.5 µm. In an alternate embodiment, the average diameter of the aggregate is 4 µm. In an alternate embodiment, the average diameter of the aggregate is 4.5 µm. In an alternate embodiment, the average diameter of the aggregate is 5 µm. In an alternate embodiment, the average diameter of the aggregate is 4.5 µm. In an alternate embodiment, the average diameter of the aggregate is 5 µm. In an alternate embodiment, the average diameter of the aggregate is 5.5 µm. In an alternate embodiment, the average diameter of the aggregate is 6 µm. In an alternate embodiment, the average diameter of the aggregate is 6.5 µm. In an alternate embodiment, the average diameter of the aggregate is 7 µm. In an alternate embodiment, the average diameter of the aggregate is 7.5 µm. In an alternate embodiment, the average diameter of the aggregate is 8 µm. In an alternate embodiment, the average diameter of the aggregate is 8.5 µm. In an alternate embodiment, the average diameter of the aggregate is 9 µm. In an alternate embodiment, the average diameter of the aggregate is 9.5 µm. In an alternate embodiment, the average diameter of the aggregate is 10 µm. In an alternate embodiment, the average diameter of the aggregate is 50 µm. In an alternate embodiment, the average diameter of the aggregate is 100 µm. In an alternate embodiment, the average diameter of the aggregate is 150 µm. In an alternate embodiment, the average diameter of the aggregate is 200 µm. In an alternate embodiment, the average diameter of the aggregate is 250 µm. In an alternate embodiment, the average diameter of the aggregate is 300 µm. In an alternate embodiment, the average diameter of the aggregate is 350 µm. In an alternate embodiment, the average diameter of the aggregate is 400 µm. In an alternate embodiment, the average diameter of the aggregate is 450 µm. In an alternate embodiment, the average diameter of the aggregate is 500 µm. In an alternate embodiment, the average diameter of the aggregate is 550 µm. In an alternate embodiment, the average diameter of the aggregate is 600 µm. In an alternate embodiment, the average diameter of the aggregate is 700 μm. In an alternate embodiment, the average diameter of the aggregate is 800 μm. In an alternate embodiment, the average diameter of the aggregate is 900 μm. In an alternate embodiment, the average diameter of the aggregate is 1 mm. In an alternate embodiment, the average diameter of the aggregate is 2 mm. In an alternate embodiment, the average diameter of the aggregate is 3 mm. In an alternate embodiment, the average diameter of the aggregate is 4 mm. In an alternate embodiment, the average diameter of the aggregate is 5 mm. In an alternate embodiment, the average diameter of the aggregate is 6 mm. In an alternate embodiment, the average diameter of the aggregate is 7 mm. In an alternate embodiment, the average diameter of the aggregate is 8 mm. In an alternate embodiment, the average diameter of the aggregate is 9 mm. In an alternate embodiment, the average diameter of the aggregate is 10 mm.

Referring to FIG. 1, a representation of solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) according to some embodiments of the present invention is shown.

In one embodiment, the surface of the solid particles may be functionalized with at least one terminal cyclocarbonate group attached to the surface via a linker, wherein the at least one terminal cyclocarbonate group and the linker has the structure set forth in formula (I) by any method readily selected by one of ordinary skill in the art. For example, the surface of the solid particles may be functionalized via a condensation reaction of a silane derivative onto silica gel. An exemplary condensation reaction is set forth in Example 1 and FIG. 2.

The conditions of the condensation reaction may be varied to achieve a certain density of the at least one terminal cyclocarbonate group attached to the surface of the solid particles. Conditions that may be varied include, but are not limited to the solvent, to the catalyst, to the concentration of the reactants, the efficiency of the reaction, the temperature of the reaction, and the like.

In one embodiment, the density of the at least one terminal cyclocarbonate group attached to the surface via a linker is one terminal cyclocarbonate group attached to the surface via a linker per $nm^2$. In some embodiments, the density is less than one terminal cyclocarbonate group attached to the surface via a linker per $nm^2$. For example, the density may be 0.9, or 0.8, or 0.7, or 0.6, or 0.5, or 0.4, or 0.3, or 0.2, or 0.1, or 0.05, or 0.04, or 0.03, or 0.02, or 0.01 terminal cyclocarbonate groups attached to the surface via a linker per $nm^2$.

In one example, the surface of the solid particles may be functionalized with at least one terminal cyclocarbonate group attached to the surface via a linker, wherein the at least one terminal cyclocarbonate group and the linker has the structure set forth in formula (I) according to the methods disclosed in Brinker, C. J., Journal of Non-Crystalline Solids 100 (1988), pg 31-50.

In another example, the surface of the solid particles may be functionalized with at least one terminal cyclocarbonate group attached to the surface via a linker, wherein the at least one terminal cyclocarbonate group and the linker has the structure set forth in formula (I) according to the methods disclosed in Graffius, Gabriel C., "Functionalization of Metal Oxide Surfaces through Chemical Reactions and Physical Adsorption" (2016). Seton Hall University Dissertations and Theses (ETDs). Paper 2150.

In another example, the surface of the solid particles may be functionalized with at least one terminal cyclocarbonate group attached to the surface via a linker, wherein the at least one terminal cyclocarbonate group and the linker has the structure set forth in formula (I) according to the methods disclosed in Kim, S., "Surface Modification of Metal Oxide Nano Particles by Capillary Condensation and its Application" (2006). PhD Thesis, University of Maryland, College Park.

In another example, the surface of the solid particles may be functionalized with at least one terminal cyclocarbonate group attached to the surface via a linker, wherein the at least one terminal cyclocarbonate group and the linker has the structure set forth in formula (I) according to the methods disclosed in Kim, S. & Ehrman, S. H., "Capillary Condensation onto Titania ($TiO_2$) Nanoparticle Agglomerates" Langmuir (2007), 23: 2497-2504.

Compositions Comprising the Solid Particles Suitable for use in Some Embodiments of the Present Invention, and Uses Thereof In one embodiment, the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) neutralize malodors produced from ammonia, primary amines and/or secondary amines.

Accordingly, in one embodiment, the present invention provides for the use of the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) to neutralize malodors produced from ammonia, primary amines and/or secondary amines Without intending to be limited to any particular theory, the use of the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) according to some embodiments of the present invention enables the efficient decrease or suppression the amount of malodor, in particular, the ammonia and primary or secondary amines responsible of malodors.

In the context of the present invention, "neutralizer" or "neutralizing" is referring to a particular mechanism including chemical and/or physico-chemical interaction with the identified malodor compounds.

Advantageously the terminal cyclocarbonate groups of the functionalized surface of the solid particles bind irreversibly with the ammonia and primary or secondary amines responsible for the malodor, leading to a drop of the concentration of the ammonia and primary or secondary amines in the surrounding environment. Unexpectedly, the perception of malodors using the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) according to some embodiments of the present invention, decreases or suppresses the malodor more rapidly than compositions lacking the solid particles according to some embodiments of the present invention.

In some embodiments, the decrease or suppression is perceived as soon as the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) are introduced to a source of malodor.

By the term primary amines or secondary amines, it is meant the normal meaning in the art, i.e. primary amine functional groups wherein a nitrogen atom is substituted by two hydrogen atoms and one hydrocarbyl group and secondary amine functional groups wherein a nitrogen atom is substituted by one hydrogen atoms and two hydrocarbyl groups. Non-exhaustive examples of the primary or secondary amines which are known to be present in malodor complex mixtures are 3-methylbutylamine, butan-1-amine, 1,5-diaminopentane or 1,4-diaminobutane.

According to any one of the above embodiments of the invention, the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) may be used in combination with compounds or technologies known to reduce or suppress the malodor perception having the same or different mode of action than compounds of the present invention. As non-limiting example, the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) may be used in combination with an absorbent material such as a material obtained from the processed corncob as described in EP1145723, or, alternatively, with the malodor counteracting composition as disclosed in WO2008155683.

In an alternate embodiment, the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) may be used in combination with a malodor counteracting (MOC) composition comprising at least one ingredient selected from Group (I) compounds, at least one ingredient selected from Group (II) compounds, and at least one ingredient selected from Group (III) compounds, wherein the Groups (I) to (III) compounds are defined as follows:
  a) Group (I): aldehydes of formula $R^1CHO$, wherein $R^1$ is an aliphatic linear or branched, saturated or unsaturated carbon chain containing from 1 to 12 carbon atoms;
  b) Group (II): ketones of formula $R^2COR^3$, wherein $R^2$ is an ethyl or methyl group and $R^3$ is an aliphatic linear or branched, saturated or unsaturated carbon chain containing from 1 to 12 carbon atoms;
  c) Group (III): primary alcohols of formula $R^4CH_2OH$, wherein $R^4$ is an aliphatic linear or branched, saturated or unsaturated carbon chain containing 1 to 12 carbon atoms, optionally substituted with an aromatic moiety.

As shown in the examples below, the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) are able to neutralize malodors in particular from ammonia and primary or secondary amines more rapidly than compounds known from the prior art and so have a better impact on the corresponding malodor. Without being bound by theory, it is believed that the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) react with the odorous amine compound forming β- or γ-hydroxy-urethane moiety. Again, without intending to be limited to any particular theory, the amines are irreversibly covalently bonded and so the concentration of the malodorous amines in the surrounding environment decreases.

In another aspect, the invention concerns the use of solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) described above in a malodor neutralizing composition or a malodor neutralizing consumer product for neutralizing malodor generated in particular by ammonia and primary or secondary amines.

In one embodiment, the present invention provides a composition comprising:
  a) solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I); and
  b) at least one ingredient selected from the group consisting of a carrier, a perfumery ingredient, a perfumery adjuvant and a mixture thereof;
    wherein the composition neutralizes malodors produced from ammonia, primary amines and/or secondary amines.

In one embodiment, the composition further comprises a malodor counteracting composition.

In one embodiment, the composition is formulated as a consumer product, wherein the consumer product neutralizes malodors produced from ammonia, primary amines and/or secondary amines.

The term "carrier" as used herein refers to a material which is neutral from a perfumery point of view i.e. that does not significantly alter the organoleptic properties of perfuming ingredients. Said carrier may be a liquid or a solid.

Non limiting examples of liquid carriers include a solubilizing system, i.e. a solvent and a surfactant system (non-ionic, anionic, cationic, amphoteric or mixtures of), or a solvent commonly used in perfumery. A detailed description of the nature and type of solvents commonly used in perfumery cannot be exhaustive. However, one can cite as non-limiting examples solvents, such as propylene glycol, glycerol, butanediol, 1,2-pentanediol, 1,2-hexanediol, hexylene glycol, 1,2-isopropylidene glycerol, dipropyleneglycol, 2-(2-ethoxyethoxy)-1-ethanol (carbitol). For the compositions which comprise both a perfumery carrier and a perfumery co-ingredient, other suitable perfumery carriers than those previously specified, can be also ethanol, water, water/ethanol mixtures, propylene glycol, limonene or other terpenes, isoparaffins such as those known under the trademark Isopar® (origin: Exxon Chemical) or glycol ethers and glycol ether esters such as those known under the trademark Dowanol® (origin: Dow Chemical Company).

Non limiting examples of solid carriers include absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualitat, Behr's Verlag GmbH & Co., Hamburg, 1996.

Encapsulation is a well-known process to a person skilled in the art, and may be performed, for instance, using techniques such as spray-drying, agglomeration or yet extrusion; or consists of a coating encapsulation, including coacervation and complex coacervation technique. Another solid carried may be an absorbent material obtained from the processed corncob as described in EP1145723. This carrier is a mixture of cellulose, hemicellulose and lignin and is formed by particles obtainable from a ring or fraction of a corncob having a content of less than 1% of fines by weight and a moisture content below 10% wherein the ring or fraction is selected from the group consisting of the woody ring with a particle size ranging between 250 and 2380 microns, the chaff ring with a particle size ranging between 73 and 841 microns, and a combination thereof.

A "perfuming ingredient" is a compound, which is of current use in the perfumery industry, i.e. a compound which is used as active ingredient in perfuming preparations or compositions in order to impart a hedonic effect. In other words, such a perfuming ingredient must be recognized by a person skilled in the art of perfumery as being able to impart or modify in a positive or pleasant way the odor of a composition, and not just as having an odor. For the sake of clarity, the definition of a perfuming ingredient is meant to include also compounds that do not necessarily have an odor but are capable of modulating the odor, e.g. masking or neutralizing unpleasant odors. For the sake of clarity, the definition of perfuming ingredient is meant to include also pro-perfumes, i.e. compounds which upon decomposition liberate a perfuming ingredient. A "perfuming composition" is a mixture of compounds including at least two perfuming co-ingredients.

In general terms, these perfuming ingredients belong to chemical classes as varied as alcohols, lactones, aldehydes, ketones, esters, ethers, ester nitriles, terpenoids, nitrogenous or sulphurous heterocyclic compounds and essential oils, and said perfuming ingredients can be of natural or synthetic origin. Specific examples of such perfuming ingredients can be found in reference texts such as the book by S. Arctander, "Perfume and Flavor Chemicals", published by the author, Montclair (New Jersey, USA), 1969, or its more recent versions, or in other work of a similar nature, as well as in the abundant patent literature in the field of perfumery. They are well known to the person skilled in the art of perfuming consumer products, that is, of imparting a pleasant odor to a consumer product.

According to any one of the above embodiments, the perfuming ingredients do not comprise a primary or secondary amino functional group.

The term "perfumery adjuvant" as used herein refers to an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art. However, one may cite as specific non-limiting examples the following: viscosity agents (e.g. surfactants, thickeners, gelling and/or rheology modifiers), stabilizing agents (e.g. preservatives, antioxidant, heat/light and or buffers agents), colour agents (e.g. dyes and/or pigments), pH regulator.

An invention's composition consisting of the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) and at least one carrier represents a particular embodiment of the invention. By malodor counteracting composition, it is meant a composition that does not comprise the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I), but which provides some malodor counteractancy and can be used to complement the neutralizing effect provided by the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I). Examples of such compositions are provided here-above.

According to a particular embodiment, the invention's composition comprises the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) as defined above in an amount comprised between 0.1% and 50% by weight, relative to the total weight of the composition and at least one solid carrier as defined above.

In one embodiment, the solid carrier is an absorbent material obtained from the processed corncob. Furthermore, the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) as defined above or a malodor composition comprising the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) can also be advantageously used in consumer products in particular perfumed consumer products to prevent the malodor formation and/or to positively impart or modify the odor of a consumer product and into which said compound of formula (I) as defined above are added.

As shown in the examples below, the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) neutralize or eliminate the odor from ammonia, primary and secondary amines.

Consequently, another object of the present invention is represented by a malodor neutralizing consumer product comprising, as malodor counteracting compound, compound of formula (I) as defined above.

For the sake of clarity, it has to be mentioned that, by "malodor neutralizing consumer product" it is meant a consumer product which is expected to deliver at least malodor counteractancy when applied to the surface to which it is applied (e.g. hair, textile, or home surface) or in the ambient air. In other words, such consumer product according to the invention is a product which comprises the functional formulation, a perfume, as well as optionally additional benefit agents, corresponding to the desired consumer product, e.g. a detergent or an air freshener, and an olfactive effective amount of the solid particles having a surface functionalized with a terminal cyclocarbonate group having at least one structure set forth in formula (I). For the sake of clarity, said consumer product is a non-edible product.

The nature and type of the constituents of the consumer product do not warrant a more detailed description here, which in any case would not be exhaustive, the skilled person being able to select them on the basis of his general knowledge and according to the nature and the desired effect of said product.

Non-limiting examples of suitable consumer product can be a fabric care product, such as a liquid or solid detergent, a fabric softener, a fabric refresher, an ironing water, a paper, a bleach, carpet cleaners or curtain-care products; a body-care product, such as a hair care product (e.g. a shampoo, a coloring preparation or a hair spray, a color care product, hair shaping product, a dental care product), a disinfectant, an intimate care product; a cosmetic preparation (e.g. a vanishing cream, a deodorant or antiperspirant, hair remover, tanning or sun product, nail products, skin cleansing or a makeup); or a skin-care product (e.g. a perfumed soap, shower or bath mousse, oil or gel, a hygiene product or foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, a furnisher care, a wipe, a dish detergent or hard-surface detergent; a leather care product or a car care product, such as a polish, waxes or a plastic cleaners; a pet product in the form of absorbent pads, litters, cleansers and refreshing and perfuming sprays and products.

In one embodiment, the consumer product can be a fabric care product, such as a liquid or solid detergent, a fabric softener, a fabric refresher, an ironing water, a hair care product such as a shampoo, a coloring preparation or a hair spray; an air care product, such as an air freshener or a "ready to use" powdered air freshener; or a home care product, such as a dish detergent or hard-surface detergent or refresher; or a malodor neutralizing sanitary product; or a pet product in the form of absorbent pads, litters, cleansers and refreshing and perfuming sprays and products. In some embodiments, the consumer product is a fabric softener, a fabric refresher, an ironing water, an air freshener, a "ready to use" powdered air freshener, a shampoo, a coloring preparation, a hair spray, or a cat litter. In one further embodiment, the consumer product is an ironing water, an air freshener, a "ready to use" powdered air freshener, a coloring preparation, or a cat litter. In one embodiment, the perfuming consumer product is an air freshener, a "ready to use" powdered air freshener, a coloring preparation or a cat litter. In one embodiment, the perfuming consumer product is an air freshener, a "ready to use" powdered air freshener or a cat litter.

The proportions in which the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) can be incorporated into the various aforementioned articles or compositions vary within a wide range of values. These values are dependent on the nature of the article and on the desired organoleptic effect as well as the nature of the co-ingredients in a given base when the microcapsules according to the invention are mixed with perfuming co-ingredients, solvents or additives commonly used in the art.

For example, in the case of malodor neutralizing compositions, typical concentrations are in the order of 0.1% to 99% by weight, alternatively from 0.1% to 80% by weight, alternatively from 0.1% to 50% by weight, alternatively from 0.1% to 20% by weight of the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) based on the weight of the composition into which they are incorporated. Concentrations lower than these, such as in the order of 0.01% to 1% by weight, can be used when the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) are incorporated into perfumed articles, percentage being relative to the weight of the article.

Formulations of consumer product bases in which the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) can be incorporated can be found in the abundant literature relative to such products. These formulations do not warrant a detailed description here, which would in any case not be exhaustive. The person skilled in the art of formulating such consumer products is able to select the suitable components on the basis of his general knowledge and of the available literature. In particular, examples of such formulations can be found in handbooks such as for example; CTFA Cosmetic ingredient handbook, $10^{th}$ edition or more recent versions; Formulating detergents and personal care products: a guide to product development (2000); as well as in the abundant patent literature in the field of body care and home care consumer products.

In one embodiment, the present invention provides a method to neutralize malodors produced from ammonia, primary amines and/or secondary amines, comprising, dispensing into a closed space in need thereof, an effective amount of solid particles having a surface functionalized with a terminal cyclocarbonate group having at least one structure set forth in formula (I) in the presence of a catalyst. Examples of catalysts suitable for use in the present invention include, but are not limited to DABCO (1,4-Diazabicyclo [2.2.2]octane), Cracac (Chromium(III) acetylacetonate), tetraethylammonium tetrafluoroborate, and the like.

In one embodiment, the present invention provides a method to neutralize malodors produced from ammonia, primary amines and/or secondary amines, comprising, dispensing into a closed space in need thereof, an effective amount of a composition comprising:
  a) solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I); and
  b) at least one ingredient selected from the group consisting of a carrier, a perfumery ingredient, a perfumery adjuvant and a mixture thereof.

In one embodiment, the composition further comprises a malodor counteracting composition.

In one embodiment, the composition is formulated as a consumer product.

In one embodiment, the present invention provides a method to neutralize malodors produced from ammonia, primary amines and/or secondary amines, comprising, applying to a surface in need thereof, an effective amount of solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I).

In one embodiment, the present invention provides a method to neutralize malodors produced from ammonia, primary amines and/or secondary amines, comprising, applying to a surface in need thereof, an effective amount of a composition comprising:
  a) solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I); and
  b) at least one ingredient selected from the group consisting of a carrier, a perfumery ingredient, a perfumery adjuvant and a mixture thereof.

In one embodiment, the composition further comprises a malodor counteracting composition.

In one embodiment, the composition is formulated as a consumer product.

The ways to dispense into the air or apply onto a surface a composition or consumer products comprising the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) are numerous. According to one embodiment, the compositions or consumer products are dispensed in a closed space by means of a device dispensing the malodor neutralizing composition comprising the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) into the air as droplets.

Devices that may introduce compositions comprising the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) to the air as droplets include: aerosol sprays, or atomizers; wall plug-ins or battery-powered devices that employ piezoelectric technology to aerosolize the composition; and, nebulization systems which disperse the liquid composition as fine droplets without the use of heat.

The aerosol spray uses a propellant and a composition comprising at least one solid particles having a surface functionalized with terminal cyclocarbonate groups of formula (I) packaged under pressure in a sealed metal or glass container with a valve which is opened by pressing down a button which contains a spray nozzle—the actuator. When the container's valve is opened by pressing the actuator, the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) is forced through the spray nozzle located inside the actuator to create a mist of droplets containing solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I). The propellant may be a liquefied gas such as propane, butane or dimethyl ether; or, it may be a compressed gas such as compressed air or compressed nitrogen.

A relatively recent type of aerosol package also suitable in the context of the invention comprises a plastic bag filled with a composition comprising solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) contained within a can. The bag is attached to the valve/actuator/spray nozzle and sealed in the can surrounded by air under pressure. When the actuator is pressed, the valve opens and the liquid composition is forced through the nozzle by the pressure around the bag.

Also suitable for the present invention are automatic aerosol dispenser devices for intermittently releasing a dose of an aerosol from an aerosol can to the surroundings. These devices generally comprise a housing, which comprises: an aerosol container containing at least one composition comprising the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) under pressure; a release mechanism adapted to release the dose of aerosol from the can to the environment when actuated; an outlet connected to the aerosol release mechanism permitting the releasing of the dose of aerosol through the housing; an actuating mechanism adapted to actuate the aerosol release mechanism intermittently; and, a timing mechanism for controlling the interval of time between actuations.

The atomizer system comprises a plastic, glass or metal container of malodor neutralizing composition comprising at least one composition comprising the solid particles of an oxide of an element selected from the group consisting of Si, Ti, Fe, Zn and Al, wherein the solid particles each have a surface functionalized with at least one terminal cyclocarbonate group attached to the surface via a linker, wherein the at least one terminal cyclocarbonate group and the linker has the structure set forth in formula (I) and a pump actuator. This operates in a similar fashion to an aerosol but the liquid composition is not packed under pressure. The pressure to atomize/aspirate the composition is created by the user of the product pressing the pump or pulling a trigger. This action creates sufficient pressure to draw the liquid stored in the container through a tube and into the actuator and spray nozzle. The mist created comprises droplets that are generally larger than those created using an aerosol spray device.

Piezoelectric technology is one of a number of electromechanical processes that exist for the generation of droplets. One method for such distribution is to atomize a liquid by a device comprising a perforated structure which is vibrated by an electromechanical transducer which has a composite thin-walled or planar structure, and is arranged to operate in a bending mode. Liquid is supplied to the vibrating perforated structure and sprayed therefrom in droplets upon vibration of the perforated structure.

Nebulizing scent delivery devices comprise an atomizer to atomize a liquid into a scented mist and deliver the scented mist to air outside of the atomizer.

According to particular embodiment, the device according to the invention is selected from the group consisting of an aerosol and an automatic aerosol spray.

According to an embodiment, the device of the invention consists of a spraying device.

EXAMPLES

The following non limiting examples are further illustrative of the present invention embodiments, and further demonstrate the advantages of the invention relative to prior art teachings.

Abbreviations have the usual meaning in the art and the temperatures are indicated in degrees centigrade (° C.).

Example 1

Figure 2:
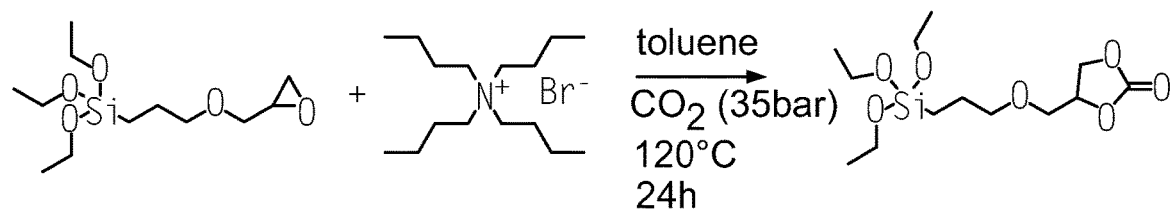
FIG. 2 shows a representation of a chemical reaction employed to generate a solid particle having a surface functionalized with terminal cyclocarbonate groups according to some embodiments of the present invention.
Figure 2:
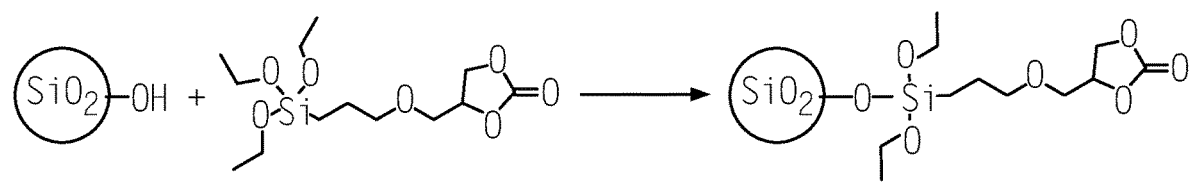

Synthesis of the Solid Particles Having a Surface Functionalized with a Terminal Cyclocarbonate Group According to Some Embodiments of the Present Invention Formation of Glycerolcarbonate Prop Yltriethoxysilane:

Referring to the reaction scheme set forth in FIG. 2, 3-Glycidoxypropyltriethoxysilane (from Fluorochem; 50 g; 180 mmol) and tetrabutylammonium bromide (1.6 g; 5.2 mmol) were dissolved in toluene (30 ml) and the solution was added to two 75 ml stainless steel autoclaves (two batches in hastelloy autoclaves). The mixtures were then purged and pressurized to 35 bar $CO_2$ and heated for 24 h at 120° C./35 bar. The autoclaves were cooled to room temperature and the remaining $CO_2$ released. The mixture was diluted with toluene, washed twice with water, once with brine, dried with anhydrous sodium sulfate, and filtered over a $SiO_2$ pad to give a transparent colorless solution. The solvent was evaporated in vacuo, to give a viscous transparent liquid.

Condensation Reaction onto Silica Particles:

Again, referring to the reaction scheme set forth in FIG. 2, 5 g of silica gel 60 were activated overnight at 150° C. under a flow of dry nitrogen. The powder was dissolved in 30 mL of toluene. 1 mL of glycerolcarbonate propyltriethoxysilane was added and the mixture was refluxed under nitrogen for 6 hours. The solid was filtered, washed with toluene once, and with ethanol twice, and dried under vacuum (20 mbar) at 40° C. overnight.

Analysis of the Solid Particles Having a Surface Functionalized with a Terminal Cyclocarbonate Group According to Some Embodiments of the Present Invention: (i) NMR:

Cyclocarbonate modified silica gel was investigated by solid state NMR. Signals in the $^{13}C$ spectrum at positions according to the monomer proved the successful reaction. $^{29}Si$ experiments showed the appearance of signals that are compatible with alkyl substituted silane groups.

Analysis of the Solid Particles Having a Surface Functionalized with a Terminal Cyclocarbonate Group According to Some Embodiments of the Present Invention: (ii) IR Spectroscopy:

The appearance of a new absorption band at 1800 cm proves the presence of a carbonyl group attached to the silica.

Example 2

Reaction with a Primary Amine in the Gas Phase:

At the bottom of a 50 mL glass vial 500 mg of silica gel particles functionalized with terminal cyclocarbonate groups was deposited. 100 µl of pure 3-methylbutylamine was added into a smaller glass vial and placed into the 50 mL vial without physical contact between the powder and the liquid. The vial was sealed and incubated for 4 h at RT. The smaller vial was then removed, and the larger vial was placed into an oven at 60° C. and a vacuum of 20 mbar was applied for 4 h to remove physically adsorbed 3-methylbutylamine.

Subsequently, 100 mg of the powder was filled into a zirconium rotor, and solid state NMR experiments were carried out. Signals in the $^{13}C$ spectrum at positions according to the amine proved the successful reaction between the 3-methylbutylamine and the terminal cyclocarbonate units at the surface of the silica particles.

Example 3

Figure 3:
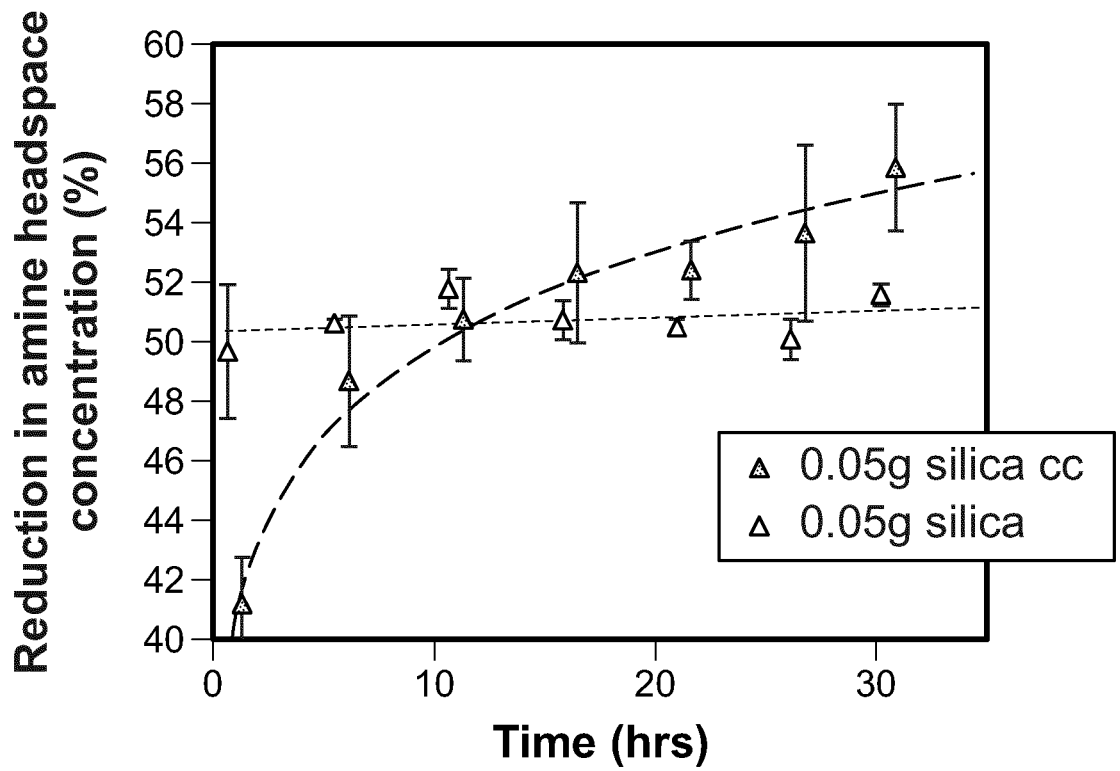
FIG. 3 shows the adsorption of 3-methylbutylamine by 0.05 g solid particles having a surface functionalized with terminal cyclocarbonate groups according to some embodiments of the present invention over time (closed triangles), compared to non-modified silica control particles (open triangles).

Adsorption of Primary Amines Using Solid Particles Having a Surface Functionalized with a Terminal Cyclocarbonate Group According to Some Embodiments of the Present Invention Into a 20 ml glass vial, 0.05 g of fumed silica HDK®N20 (Wacker Silicones) was deposited. For comparison, 0.05 g of the same silica surface modified with cyclocarbonate (labelled silica cc) was deposited in another vial. In each vial, the silica powder was mixed with 0.1 g of a solution 5% wt. 3-Methylbutylamine in dipropyleneglycol. The glass vials were hermetically closed and let to equilibrate for 1 h30 at 32° C. Using a headspace syringe, 1 ml of the gas phase in the vial was collected and injected in a GC/MS for analysis of the 3-methylbutylamine concentration. % of 3-methylbutylamine adsorbed was subsequently calculated. The operation was repeated at regular intervals over time. The whole experiment was duplicated. The results are shown in FIG. 3.

A fast equilibrium is obtained with the reference silica with a plateau in amine concentration, indicating a physical adsorption. On the other hand the adsorption by modified silica cc continuously increases over time, indicating a chemical reaction on top of physical adsorption. Adsorption with modified silica becomes higher after about 12 hours equilibration. After 30 hrs, about 56% of 3-methylbutylamine is adsorbed by modified silica cc, compared to about 52% with silica.

Figure 4:
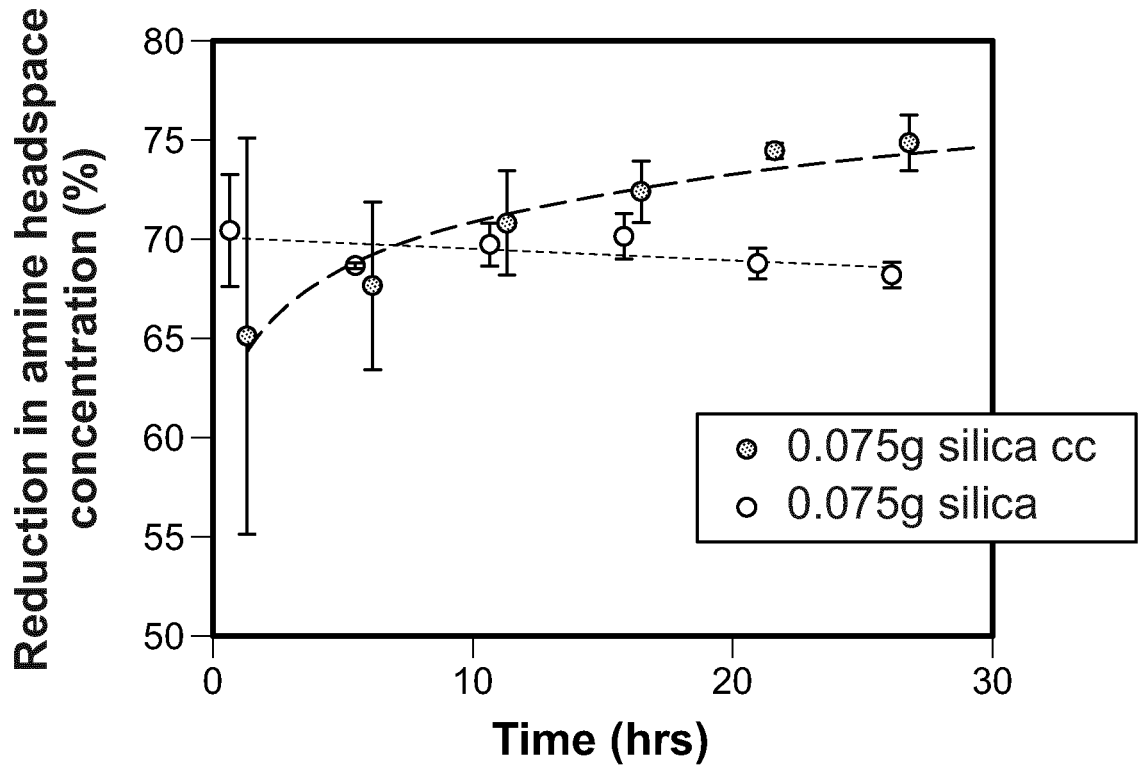
FIG. 4 shows the adsorption of 3-methylbutylamine by 0.075 g solid particles having a surface functionalized with terminal cyclocarbonate groups according to some embodiments of the present invention over time (closed circles), compared to non-modified silica control particles (open circles).

In a subsequent experiment, into a 20 ml glass vial, 0.075 g of fumed silica HDK®N20 (Wacker Silicones) was deposited. For comparison, 0.075 g of the same silica surface modified with cyclocarbonate (labelled silica cc) was deposited in another vial. In each vial, the silica powder was mixed with 0.1 g of a solution 5% wt. 3-Methylbutylamine in dipropyleneglycol. The glass vials were hermetically closed and let to equilibrate for 1 h30 at 32° C. Using a headspace syringe, 1 ml of the gas phase in the vial was collected and injected in a GC/MS for analysis of the isoamylamine concentration. % of 3-methylbutylamine adsorbed was subsequently calculated. The operation was repeated at regular intervals over time. The whole experiment was duplicated. The results are shown in FIG. 4.

The results showed a higher adsorption of 3-methylbutylamine by silica when compared to the modified silica cc over the first 10 hrs. The adsorption by modified silica cc however increases over time, to become higher after about 10 hrs equilibration. After 25 hrs, about 75% of 3-methylbutylamine is adsorbed by modified silica cc, compared to only about 67% with silica. Here again, the plateau observed with reference silica is more in relation with a physical adsorption, while a progressive chemical reaction of amino compound with silica cc results in an increasing removal of amine from the headspace over time.

Figure 5:
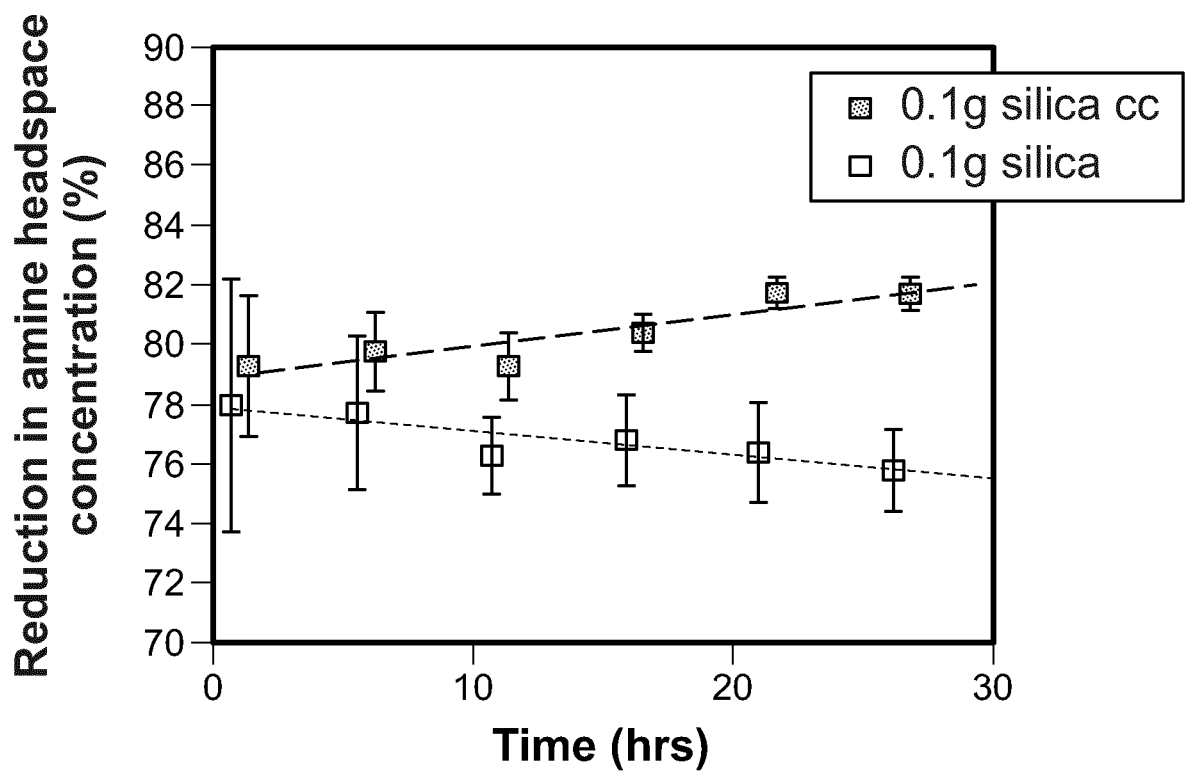
FIG. 5 shows the adsorption of 3-methylbutylamine by 0.1 g solid particles having a surface functionalized with terminal cyclocarbonate groups according to some embodiments of the present invention over time (closed squares), compared to non-modified silica control particles (open squares).

In a subsequent experiment, into a 20 ml glass vial, 0.1 g of fumed silica HDK®N20 (Wacker Silicones) was deposited. For comparison, 0.1 g of the same silica surface modified with cyclocarbonate (labelled silica cc) was deposited in another vial. In each vial, the silica powder was mixed with 0.1 g of a solution 5% wt. 3-Methylbutylamine in DiPG. The glass vials were hermetically closed and let to equilibrate for 1 h30 at 32° C. Using an headspace syringe, 1 ml of the gas phase in the vial was collected and injected in a GC/MS for analysis of the 3-methylbutylamine concentration. % of 3-methylbutylamine adsorbed was subsequently calculated. Operation was repeated at regular intervals over time. The whole experiment was duplicated. The results are shown in FIG. 5. The results showed a higher adsorption of 3-methylbutylamine by modified silica cc when compared to the modified silica cc after 1 h30. The adsorption by modified silica cc increases over time, to reach about 82% of 3-methylbutylamine adsorbed, compared to only about 76% with silica. Same observations with regards to the shape of the curves can be made when compared to previous results.

Example 4

Synthesis of the Solid Particles Having a Surface Functionalized with a Terminal Cyclocarbonate Group According to Some Embodiments of the Present Invention Formation of Glycerolcarbonate Propyltrimethoxysilane:

Referring to the reaction scheme set forth in FIG. 2, 3-Glycidoxypropyltrimethoxysilane (from Sigma; 8.15 g; 34.5 mmol) and tetrabutylammonium bromide (0.33 g; 1.03 mmol) were dissolved in toluene (21 ml) and the solution was added to two 75 ml stainless steel autoclaves (two batches in hastelloy autoclaves). The mixtures were then purged and pressurized to 35 bar $CO_2$ and heated for 24 h at 120° C./35 bar. The autoclaves were cooled to room temperature and the remaining $CO_2$ released. The mixture was diluted with toluene, washed twice with water, once with brine, dried with anhydrous sodium sulfate, and filtered over a $SiO_2$ pad to give a transparent colorless solution. The solvent was evaporated in vacuo, to give a viscous transparent liquid.

Condensation Reaction onto Silica Particles:

Again, referring to the reaction scheme set forth in FIG. 2, 2.5 g of silica gel Sipernat 2000 were dispersed in 13 g of deionized water and 8 g of absolute ethanol. One drop of concentrated hydrochloric acid was added and the mixture was stirred at 60° C. 0.5 mL of glycerolcarbonate propyltrimethoxysilane was added and the mixture was stirred at 60° C. for 90 minutes. The solvent was removed until dryness, the residue was then washed with toluene twice, filtered, and dried under vacuum (20 mbar) at 40° C. overnight. The successful reaction was confirmed by $^{29}Si$ and $^{13}C$ solid state NMR spectroscopy.

Example 5

Reaction with a Primary Amine in Liquid Phase:

0.5 g of the solid particles having a surface functionalized with a terminal cyclocarbonate group was dispersed in 5 g of absolute ethanol. 80 µl of pure 3-methylbutylamine was added. The vial was sealed and stirred for 3 h30 at RT. The mixture was filtered, and the functionalized silica powder was dried under vacuum of 20 mbar for 4 h to remove physically adsorbed 3-methylbutylamine Subsequently, 100 mg of the powder was filled into a zirconium rotor, and solid state NMR experiments were carried out. Signals in the 13C spectrum at positions according to the amine proved the successful reaction between the 3-methylbutylamine and the terminal cyclocarbonate units at the surface of the silica particles.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

The invention claimed is:

1. A composition comprising solid particles of an oxide of an element selected from the group consisting of Si, Ti, Fe, Zn and Al and at least one solid carrier, wherein the solid particles each have a surface functionalized with at least one terminal cyclocarbonate group attached to the surface via a linker, wherein the at least one terminal cyclocarbonate group and the linker has the structure set forth in formula (I):

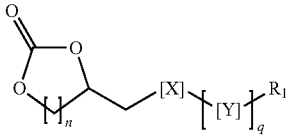

wherein:
n=1 or 2;
[X] is an element selected from the group consisting of O, N and C;
[Y] represents an alkylene group carrying 1-20 C atoms, that can be linear, branched, or cyclic, or connected to a carbonyl or an ether group;
q=0 or 1; and
$R_1$ is a coupling reactive group serving as a linker selected from silanes, siloxanes, phosphates or carboxylates,
wherein the composition comprising the solid particles in an amount comprised between 0.1% and 50% by weight, relative to the total weight of the composition, wherein the solid carrier is an absorbent material obtained from a processed corncob.

2. The composition of claim 1, wherein n=1, [X] is O, [Y] is propylene, q=1, and $R_1$ is tri(m)ethoxysilane.

3. The composition of claim 1, wherein the solid particles are chosen from the group of silica particles.

4. The composition of claim 1, wherein the structure set forth in formula (I) is a single structure.

5. The composition of claim 1, further comprising at least one ingredient selected from the group consisting of a carrier, a perfumery ingredient, a perfumery adjuvant and a mixture thereof.

6. The composition of claim 1, further comprising a malodor counteracting composition.

7. The composition of claim 6, wherein the malodor counteracting composition comprises at least one ingredient selected from a Group (I) of compounds, at least one ingredient selected from a Group (II) of compounds, and at least one ingredient selected from a Group (III) of compounds, wherein the Groups (I) to (III) compounds are defined as follows:
a) Group (I): aldehydes of formula $R^1CHO$, wherein $R^1$ is an aliphatic linear or branched, saturated or unsaturated carbon chain containing from 1 to 12 carbon atoms;
b) Group (II): ketones of formula $R^2COR^3$, wherein $R^2$ is an ethyl or methyl group and $R^3$ is an aliphatic linear or branched, saturated or unsaturated carbon chain containing from 1 to 12 carbon atoms;
c) Group (III): primary alcohols of formula $R^4CH_2OH$, wherein $R^4$ is an aliphatic linear or branched, saturated or unsaturated carbon chain containing 1 to 12 carbon atoms, optionally substituted with an aromatic moiety.

8. The composition of claim 1, wherein the composition is formulated as a fabric care product, a body-care product, a skin-care product, an air care product, a pet care product or a home care product.

9. The composition of claim 8, wherein the composition is formulated as a fabric softener, a fabric refresher, an ironing water, an air freshener, a "ready to use" powdered air freshener, a shampoo, a coloring preparation, a hair spray, or a cat litter.

10. A method to neutralize malodors produced from ammonia, primary amines and/or secondary amines, the method comprising dispensing into a closed space in need thereof, an effective amount of the composition recited in claim 1.

11. A method to neutralize malodors produced from ammonia, primary amines and/or secondary amines, the method comprising applying to a surface in need thereof, an effective amount of the composition recited of claim 1.

* * * * *